United States Patent [19]

Patel et al.

[11] Patent Number: 5,627,149
[45] Date of Patent: May 6, 1997

[54] COMPOSITION

[75] Inventors: Amrit Patel; Suman K. Chopra, both of Dayton, N.J.

[73] Assignee: Colgate Palmolive Company, New York, N.Y.

[21] Appl. No.: 340,918

[22] Filed: Nov. 17, 1994

[51] Int. Cl.$^6$ .............................. C11D 1/02; C11D 1/22; C11D 1/62; C11D 3/37

[52] U.S. Cl. ................ 510/125; 510/127; 510/129; 510/119; 510/158; 510/159; 510/417; 510/418; 510/423; 510/424; 510/426; 510/427; 510/433; 510/475; 510/496; 510/504

[58] Field of Search .................................. 252/547, 558, 252/174.23, DIG. 5; 510/125, 127, 129, 119, 158, 159, 417, 418, 423, 424, 426, 427, 433, 475, 496, 504

[56] References Cited

U.S. PATENT DOCUMENTS

| | | | |
|---|---|---|---|
| 3,288,770 | 11/1966 | Butler | 526/204 |
| 3,903,008 | 9/1975 | DeWeever et al. | 252/118 |
| 4,000,077 | 12/1976 | Wixon | 252/8.75 |
| 4,240,450 | 12/1980 | Grollier et al. | 132/7 |
| 4,303,543 | 12/1981 | Mansy | 252/117 |
| 4,501,834 | 2/1985 | Su | 524/28 |
| 4,673,525 | 6/1987 | Small et al. | 252/132 |
| 4,888,119 | 12/1989 | Klewsaat | 252/8.75 |
| 4,913,828 | 4/1990 | Caswell et al. | 252/88 |
| 4,919,839 | 4/1990 | Durbut et al. | 252/153 |
| 5,415,812 | 5/1995 | Durbut et al. | 252/547 |

FOREIGN PATENT DOCUMENTS

| | | |
|---|---|---|
| 0015032 | 9/1980 | European Pat. Off. . |
| 0294892 | 12/1988 | European Pat. Off. . |
| 1050791 | 12/1966 | United Kingdom . |

Primary Examiner—Michael P. Tierney
Attorney, Agent, or Firm—Martin B. Barancik

[57] ABSTRACT

A method for preparing an aqueous fluid personal care composition having an anionic surfactant and a cationic surfactant and/or polymer therein which comprises:

a. contacting at least about 0.2 mole % of the anionic surfactant with a charge neutralizing amount of a cationic surfactant and/or polymer in a reactor and forming an essentially chargeless complex in the reactor which is essentially free of other components of the said composition, and b. thereafter mixing the preformed complex with the remainder of the composition components.

5 Claims, No Drawings

COMPOSITION

BACKGROUND OF THE INVENTION

Throughout the years there have been continuing methods of improving the characteristics such as foam, conditioning effects and other properties of personal care compositions for hair and/or skin particularly in the fluid forms, for example liquid, gel or emulsion. A new approach for improving various of the above properties has now been discovered.

In the past there have been complexes made between soap and cationic polymers in order to increase the mildness of the solid composition see WO 93/06205. However in that patent application, there is nothing mentioned about any positive attributes that such a complex may provide to the finished solid composition. It is only stated that there is equivalent "tightness" when the complex of the cationic polymer with soap is present in comparison to the solid composition bar when there is no complex present. Furthermore the document states that such complex between the soap and the cationic polymer does not adversely affect bar smear, wear rate, lather, or rinsing profile. When the cationic polymer was provided alone to the bar composition as opposed to present in a complexed state with the soap, the bar demonstrated significant reduction in dryness and redness compared to the bar without cationic polymer. However the bar had a significant increase in tightness.

BRIEF SUMMARY OF THE INVENTION

In accordance with the invention there is an aqueous fluid personal care composition comprising:

a. a cationic surfactant and/or polymer complexed with an anionic surfactant and b. one or more non complexed anionic surfactants said composition essentially free of other complexes wherein a different anionic surfactant is employed.

DETAILED DESCRIPTION OF THE INVENTION

It has now been found that the formation of a complex between a cationic surfactant and/or polymer and an anionic surfactant brings about increased properties to an aqueous fluid personal care composition. Conditioning, positive moisturizing effects and better foam properties can individually or in combination(s) be observed as well as lather enhancement when the complex of cationic surfactant and/or polymer and anionic surfactant is present in the personal care composition.

Anionic surfactants which can form the complex with the cationic surfactant and/or polymer include soaps, i.e. long chain alkyl carboxylate salts, sulfonates, alkylaromatic sulfonates such as dodecylbenzene sulfonate, secondary alkyl sulfonates, alpha olefin sulfonates, alkyl glyceryl ether sulfonates, primary and secondary alkyl sulfates, alkyl ether sulfates, fatty acid amide sulfonates, phosphates, taurates, sulfosuccinates, isethionates, such as sodium cocoyl isethionate (SCI) and the like. Many of these anionic surfactants can be alkoxylated preferably ethoxylated, such as the carboxylate, sulfate, ether sulfates, sulfonates, glyceryl sulfonates and the like. Also included within the definition of anionic surfactants for the purpose of this specification and claims are anionic substances which are classified as hydrotropes. These materials are also known to remove soil from surfaces. Some of these are classified as surfactant—hydrotrope in the Cosmetic Toiletry Fragrance Association, International Cosmetic Ingredient Dictionary, 4th Edition, 1991, hereafter referred to as CTFA), for example a salt of cumene sulfonate, i.e. sodium salt. Other examples of such hydrotropic materials are xylene sulfonates, toluene sulfonate (essentially the short chain alkyl substituted aromatics) and substituted carboxylated cocoimidazoline organophosphate, available as Phosphoteric P-C6 from Mona Industries.

Particular anionic surfactants which can be complexed are soaps, sulfonates such as alkyl glyceryl ether sulfonates, ethoxylated or not, sodium cocoyl isethionate (SCI), sodium cocoylmonoglyceryl sulfonate (CMGS), sodium lauryl sulfate, ethoxylated or not, the short chain alkyl substituted aromatic, particularly sodium cumene sulfonate, ethoxylated or not, and the like.

Cationic surfactants or polymers which can be employed include surfactants, for example ammonium salts such as distearyldimethylammonium chloride, halide salts of methylated ammonium wherein at least one and preferably two or three of the groups on the nitrogen are long chain substantially saturated material such as tallow fatty radicals, hydrogenated tallow fatty radicals, methosulfate anionic salts of the above, long chain amidoderivative such as mink oil amidopropyldimethyl-2-hydroxyethylammonium chloride (Quaternium 26), aromatics such as isododecylbenzyl triethanol ammonium chloride, N-alkylated amphoteric materials such as N-alkylated betaines. Further cationic surfactants can include alkylamines, alkyl imidazolines, various ethoxylated amines and the like. Examples of such cationic surfactants as noted in the CTFA include Quaternium-8, -14, -18, -24, -26, -27, -33, -43, -52, -53, -60, -62, -83 and the like. Cationic surfactants which are monomeric as opposed to polymeric surfactants are preferred. The presence of multiple alkoxy groups does not make a monomeric cationic surfactant a polymeric material for purposes of the specification and claims. Examples of cationic polymers include the polymerized materials such as certain quaternary ammonium salts, copolymers of various materials such as hydroxyethyl cellulose and dialkyldimethyl ammonium chloride, acrylamide and beta methacryloxyethyl trimethyl ammonium methosulfate, the quaternary ammonium salt of methyl and stearyl dimethylaminoethyl methacrylate quaternized with dimethyl sulfate, quaternary ammonium polymer formed by the reaction of diethyl sulfate, a copolymer of vinylpyrrolidone and dimethyl aminoethylmethacrylate, quaternized guars and guar gums and the like. Exemplary of cationic polymers which can be used to make the complexes of this invention include, as disclosed in the previously referred to CTFA, Polyquaternium-1,-2, -4, -5, -6, -7, -8, -9, -10, -11, -12, -13, -14, -15, -16, -17, -18, -19, -20, -22, -24, -27, -28, -29 and -30.

A designed procedure to bring about the complexing of cationic material and anionic surfactant is required as opposed to the random mixing of all formulation components together at the same time. The latter procedures can bring about a mixture of complexes and does not ensure the preparation of a single, meaningful complex so as to properly affect properties. For example, in accordance with the invention, the cationic material and anionic surfactant desired to be complexed can be mixed together in the presence of water in a Ross mixer at room temperature or an elevated temperature for 15 to 30 minutes prior to contact of either material with any other component present in the final personal care composition. The remainder of the material present in the composition such as, for example, anionic surfactant is then added and the admixture stirred at elevated temperature. Soap, if present in the final formulation and not already complexed if desired to do so, can then be added and the mass further mixed. Therefore it is clear that the complex of the invention is made separately from the ordinary personal care composition manufacturing process and is present in the final composition as a preformed complex. It is important to note that the complex is not charged, essentially neutral.

The quantity of complex, or precomplex, which can be interchangeably used throughout the specification and claims for complex, showing that it is purposefully made, is present up to about 25 mole percent of the anionic surfactant present. Little advantageous behavior is seen for having more than about 25 mole % of the anionic surfactant complexed with the cationic surfactant and/or polymer unless there is an unusually small amount of anionic surfactant present. Generally at least 0.2 mole % of the anionic surfactant should be complexed to observe beneficial effects. Preferably above about 0.5 or 1 mole % of the anionic surfactant present should be complexed with the cationic material. A range of about 2 to about 15 mole % of the anionic surfactant is preferably complexed with the cationic surfactant, more preferably up to about 10 or 5 mole % maximum. Generally, the complex formation occurs on a one to one molar or equivalent basis.

Other materials commonly found in personal care fluid compositions can be present in the final formulation. For example nonionic surfactants such as long chain ethanolamine amides and alkyl polyglycosides can also be present in the composition. Various preservatives, chelating agents, antibacterial agents, pigments, dyes, fragrances, free fatty acids, extra cationic surfactants and/or polymers and the like can also be present in the solid compositions. They may be added at their usual position in the manufacturing process.

The final fluid composition can take any fluid form such as liquid, gel, emulsion, two or more fluid phases or even have a solid phase therein as long as it is readily dispersible within the fluid phase. The fluid composition can be used as aqueous based shampoos, shower gel, 2 in 1 shower emulsion and the like. The complex within the formulation can be totally soluble therein, partially soluble or essentially non-soluble as liquid or particulate matter.

The preferred anionic surfactant employed is the short alkyl chain aromatics, particularly the cumene sulfonates. The preferred cationic materials are the cationic polymers and particularly those identified in the CTFA as Polyquaternium-6,-7, and-16. The complexes succeed in increased properties of conditioning for skin and/or hair as well as oftentimes foaming properties as well. Interestingly, similar properties to the formulation prepared by ordinary methods can be achieved by utilizing the complex but with fewer active agents present, thereby creating a cost savings for the final formulation.

The anionic surfactants can vary from about 1 to 99 wt. % of the composition, taking into account the portion of complex which is anionic surfactant as well. A preferred quantity of anionic surfactant is a minimum of 2 wt. % of the composition.

Below are procedures to prepare the complex of the cationic surfactant and/or polymers and anionic surfactant as well as formulations having such complexes therein and comparison testing to control formulations.

1. Preparation of complex.

Distearyldimethylammonium chloride was mixed with the anionic surfactant to be complexed (for example soap, SCI, sodium cumene sulfonate and the like) in an equimolar amount in the presence of water for a period of 15–30 minutes in a Ross mixer at 100°–110° C. The cationic and anionic surfactant complex made by this process were studied by differential scanning calorimetry (DSC). These complexes have different melting points/softening points than the individual starting materials. In like manner various anionic surfactants such as ammonium lauryl sulfate, alpha olefin sulfonate, sodium benzene sulfonate, SCI, sodium cumene sulfonate, sodium deceth-3-sulfate, sodium laureth-2EO sulfate, sodium cocoate and sodium tallowate were combined with cationic materials such as cetrimonium chloride, distearyl diammonium chloride, tricetyl ammonium chloride, polyquatrium-6,-7, and -16 and complexes made. Cationic materials that are liquid at room temperature do not generally require heating. The reaction generally occurs on a molar or equivalent basis. Where cationic polymers are used, the quantity of material employed in the reaction is dependent upon the change density of the polymer. As stated previously, the preformed complex present in the final formulation is at least essentially neutral. Preferably it bears no charge.

In the example below, the following procedure was followed. After the complex was prepared, 1 wt. % of the 1:1 (neutral) complex was dissolved in 10 wt. % aqueous sodium laureth (2) sulfate solution. The following test method was employed.

Pre-Treatment of Approx. 3.2 g Tresses

1. Run tap water until a constant temperature of 105° C. is obtained.
2. Thoroughly wet all tresses.
3. Using a hypodermic syringe or squirt/wash bottle, place approximately 3 cc of a freshly prepared 15% aqueous solution of Sodium Laureth 2EO Sulfate on the tress.
4. Work this solution through the hair with an up and down motion for 60 seconds, evenly coating the hair. Be certain to reach to top (root) end, as well as the tip end. Rinse for thirty seconds.
5. Repeat steps 2 and 3 for all tresses, rinsing for as long as necessary to remove all lather.

Treatment

1. Using random, non-repeating letters, code tresses with non-water soluble marker or tape; a minimum of 2 tresses will be required for each product tested, if statistical results are expected.
2. Using a hypodermic syringe, place 1 cc of the test shampoo on the tress.
3. Work the tress between the fingers in an up and down motion for one minute, evenly coating the hair. Be certain to reach to top (root) end, as well as the tip end.
4. Rinse thoroughly for 60 seconds under 105° C. tap water.
5. Repeat steps 2 and 4 for each tress.
6. Rinse thoroughly for 60 seconds under 105° C. tap water.

Pre-Evaluation

1. Using a non-water soluble marker or tape, designate and code a comb for each tress.
2. Keeping each comb with its designated tress, gently comb through snags, first with wide teeth, then narrow. This is to avoid difficulty during the ranking process.

Wet Combing Evaluations

1. Hang coded tresses and corresponding combs above trough, sink, or paper towels.
2. Arrange tresses/combs in random orders and maintain wet with Deionized Water, using a wash- or trigger-squirt bottle, sufficient to drip lightly.
3. Call expert judges, one at a time, to comb tresses:
   a. Using fine teeth of the comb, judges should comb tresses, move them, and place them in descending order from easiest-to-hardest to comb. The tresses are then called Ranked.

b. Record Rank order. No Rank should be repeated.

c. Have judges assign a rating from 1 to 10 to each tress, 10 being easiest to comb, using their own internal definitions of what 1 to 10 is. Duplicate Ratings are allowed.

d. Record Rate order of each tress corresponding to its Rank.

e. Re-randomize tresses/combs.

4. Repeat step 3 until all judges have combed tresses.

In the results below, the following abbreviations are used:

Anionic

SCS is sodium cumene sulfonate
ALS is ammonium laureth (2) sulfate
SLES is sodium laureth (2) sulfate
AOS is $C_{14}$–$C_{15}$ alpha olefin sulfonate
SBS is sodium benzene sulfonate
SDES is sodium deceth-3 sulfate
SCI is sodium cocoyl isethionate

Cationic

CTAC is cetrimonium ammonium chloride
DSDAC is distearyl di ammonium chloride
TCAC is tricetyl ammonium chloride Merquat 550 is Polyquaternium-7, available from Calgon, and is the polymeric quaternary ammonium salt consisting of acrylamide and dimethyl dialkyl ammonium chloride monomers.

Luviquat FC-905 is polyquaternium 16, available from BASF, and is a polymeric quaternary ammonium salts formed from methylvinyl-imidazolium chloride and vinylpyrrolidone.

Merquat 100 is polyquaternium-6, available from Calgon, and is a polymer of dimethyl diallyl ammonium chloride.

Below are the results:

| Anionic | Cationic | Wet Combing Evaluation |
|---|---|---|
| SCS | CTAC | 2.50 |
|  | DSDAC | 3.00 |
|  | TCAC | 3.25 |
|  | Merquat 550 | 4.00 |
|  | Luviquat FC-905 | 3.75 |
|  | Merquat 100 | 4.25 |
| ALS | CTAC | 1.50 |
|  | DSDAC | 2.00 |
|  | TCAC | 2.00 |
|  | Merquat 550 | 2.75 |
|  | Luviquat FC-905 | 2.75 |
|  | Merquat 100 | 2.70 |
| SLES | Merquat 550 | 2.50 |
|  | DSDAC | 2.00 |
| AOS | Merquat 550 | 2.50 |
|  | DSDAC | 2.00 |
| SBS | Merquat 550 | 2.75 |
|  | DSDAC | 2.00 |
| SDES | Merquat 550 | 3.00 |
|  | DSDAC | 2.75 |
| SCI | CTAC | 2.00 |
|  | Merquat 550 | 3.00 |
| - None - (Control) | CTAC | 1.00 |
|  | DSDAC | 1.00 |
|  | TCAC | 1.50 |
|  | Merquat 550 | 1.75 |
|  | Merquat 100 | 1.50 |
|  | Luviquat FC-905 | 1.50 |

As is observed from the data the best conditioning results occur with the use of cumene sulfonate as the anionic portion of the complex and the cationic polymer(s) as the cationic portion of the chargeless complex.

A precomplex of SCS and Polyquat-6, -7, and -16 was prepared by mixing 1.96 g SCS (93% active), 0.3 g Polyquat-6 (40% active), 0.2 g Polyquat-16 (40% active), and 3.5 g Polyquat-7 (8% active) with 5.0 g water and heating to 85° C. for twenty five minutes. The complexed material was then added to the same components presently used in Optims Shampoo, Nouriche® other than those in the complex marketed by Colgate-Palmolive Company. However, this final formulation had sufficiently reduced actives to have a cost greater than 10% below the presently marketed Nouriche Optims Shampoo. The performance of the reduced cost shampoo with respect to conditioning was equivalent to the presently marketed, more costly shampoo.

We claim:

1. A method for preparing an aqueous fluid personal care composition having a hydrotropic short chain alkyl aromatic sulfonate and a cationic polymer therein which comprises:

a. contacting at least about 0.2 mole % of said aromatic sulfonate with a charge neutralizing amount of a cationic polymer in a reactor and forming an essentially chargeless complex in the reactor which is essentially free of other components of the said composition, and b. thereafter mixing the preformed complex with the remainder of the composition components.

2. The method in accordance with claim 1, wherein the cationic polymer is selected from the group consisting of a polymer of dimethyl dialkyl ammonium chloride, a polymeric quaternary ammonium salt consisting of acrylamide and dimethyl dialkyl ammonium chloride monomers, and a polymeric quaternary ammonium salt of methylvinyl-imidazolium chloride and vinylpyrrolidone.

3. The method in accordance with claim 1 wherein the aromatic sulfonate is a cumene sulfonate.

4. An aqueous fluid personal care composition made by the method of claim 1.

5. An aqueous fluid personal care composition made by the method of claim 2.

* * * * *